US00PP08013P

United States Patent [19]

Bradford et al.

[11] Patent Number: Plant 8,013

[45] Date of Patent: Oct. 27, 1992

[54] NECTARINE TREE (RED JEWEL)

[76] Inventors: Lowell G. Bradford, 12439 E. Savana Rd.; Norman G. Bradford, 11875 E. Savana Rd., both of Le Grand, Calif. 95333

[21] Appl. No.: 720,212

[22] Filed: Jun. 24, 1991

[51] Int. Cl.[5] ..... A01H 5/00
[52] U.S. Cl. ..... Plt./41.3
[58] Field of Search ..... Plt./41.3

[56] References Cited

U.S. PATENT DOCUMENTS

P.P. 2,976 6/1970 Anderson ..... Plt. 41
P.P. 3,165 5/1972 Anderson ..... Plt. 41

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described during the first half of July, with first picking on Jul. 1, 1990, and the last picking on Jul. 15, 1990. The fruit is uniformly large in size, very good in flavor, attractive in appearance, freestone in type, very firm in texture, and full red in skin color. The variety originated as a second generation seedling of a cross between Red Diamond (U.S. Plant Pat. No. 3,165) and Autumn Free (U.S. Plant Pat. No. 2,976).

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Red Jewel". The present variety was originated by us in 1981 in a cultivated area of our experimental orchard at Bradford Farms near Le Grand, Calif. in Merced County (San Joaquin Valley). It was obtained by growing an open pollinated seed from an unnamed seedling. This unnamed seedling was previously developed as a cross of the selected seed parent, Red Diamond (U.S. Plant Pat. No. 3,165), and the selected pollen parent, Autumn Free (U.S. Plant Pat. No. 2,976). Subsequent to origination of the present variety of nectarine tree, we asexually reproduced it by budding and grafting, and such reproduction of plant and fruit characteristics were true to the original plant in all respects.

The present variety is similar to its selected seed grandparent, the Red Diamond (U.S. Plant Pat. No. 3,165), in fruit appearance by being a full red colored freestone nectarine with excellent firmness, but is distinguished therefrom and an improvement thereon by producing fruit that ripens 3 days later, is larger in size, is crispier in texture, and has a yellow pit cavity that tightly surrounds the stone.

The present variety differs substantially from its selected pollen grandparent, the Autumn Free Nectarine (U.S. Plant Pat. No. 2,976), by producing fruit that ripens approximately 65 days earlier and that is full red in color at harvest time.

DRAWING

The accompanying photograph exhibits four whole fruits positioned to display the characteristics of the skin color and form, one fruit divided in the axial plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jul. 8, 1990. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Shaggy.
- *Bark color.*—Dark grayish yellowish brown [81. d.gy.yBr].
- *Lenticels.*—Numerous. Color: Dark Orange yellow [72. d.OY]. Size: $\frac{1}{8}$" to $\frac{3}{8}$", [3.2–9.5 mm.].

Branches:
- *Size.*—Medium.
- *Texture.*—Medium.
- *Color.*—1st Year Wood Topside: Grayish pink [8. gy.Pk]. 1st Year Wood Underside: Brilliant yellow green [116. brill.YG]. Older Wood: Moderate yellowish brown [77. m.yBr].
- *Lenticels.*—Numerous, very small.

Leaves:
- *Size.*—Large. Average Length: $5\frac{3}{8}$" [136.5 mm.]. Average Width: $1\frac{5}{8}$" [41.3 mm.].
- *Thickness.*—Medium.
- *Form.*—Elliptical.
- *Apex.*—Acuminate.
- *Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Dorsal Color: Moderate yellow green [120. m.YG]. Ventral Color: Light yellow green [119. l.YG].

*Stipules.*—Numerous. Length: ⅛" to ⅜" [3.2-9.5 mm.].

*Glands.*—Numbers: 2 to 4 per leaf. Position: Some alternately and some oppositely positioned on petiole and base of blade. Size: Medium. Form: Reniform. Color: Brilliant yellow green [116. brill.YG].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Small.

*Color.*—Moderate pink [5. m.Pk].

FRUIT

Maturity when described: Firm and eating ripe, Jul. 8. 1990.

Date of first picking: Jul. 1, 1990.

Date of last picking: Jul. 15, 1990.

Size: Uniform, large.

*Average diameter axially.*—2 11/16" [68.3 mm.].

*Average traversely in suture plane.*—2⅞" [73.0 mm.].

Form: Uniform, slightly unsymmetrical, slightly oblong.

*Longitudinal section form.*—Oval.

*Transverse section through diameter.*—Round.

Suture: A shallow groove extending from the base to beyond the apex, becoming deeper toward the apex.

Ventral surface: Rounded, lipped throughout on both sides toward apex.

Lips: Slightly unequal.

Cavity: Flaring, elongated in the suture plane with a sharp suture mark showing on one side only.

*Depth.*—7/16" [11.1 mm.].

*Breadth.*—⅞" [22.2 mm.].

Base: Slightly truncate, with stem markings typical.

Apex: Rounded.

Pistil point: Mostly oblique, depressed within the suture, short in length on most, slightly mammiform on a few.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed as of yet.

*Color.*—A glossy dark red [16. d.R] over a vivid reddish orange [34. v.rO] background with a slight amount of brilliant orange yellow [67. brill.OY] freckling near the apex end.

Flesh:

*Color.*—Brilliant yellow [83. brill.Y] with very little moderate red [15. m.R] flecking.

*Surface of pit cavity.*—Covered with light yellow [86. l.Y] fibers.

*Amygdalin.*—Moderate.

*Juice.*—Moderate, rich.

*Texture.*—Firm, very crisp.

*Fibers.*—Abundant, fine.

*Ripens.*—Evenly.

*Flavor.*—Acidic and sweet.

*Aroma.*—Slight.

*Eating quality.*—Very good.

STONE

Type: Freestone.

Form: Oblong.

Base: Straight.

Apex: Acute.

Sides: Slightly unequal.

Surface: Irregularly furrowed toward the apex and pitted toward the base.

Ridges: Jagged toward the base.

Color: Light brown [57. l.Br].

Pit wall: 3/16" [4.8 mm.] thick.

Tendency to split: None observed.

Kernel:

*Form.*—Oval.

*Taste.*—Sweet.

*Viable.*—Yes.

*Average width.*—7/16" [11.1 mm.].

*Average length.*—13/16" [20.6 mm.].

*Color.*—Light yellow [86. l.Y] when first cracked.

*Pellicle color.*—Moderate brown [58. m.Br].

*Amygdalin.*—Scant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to its seed grandparent, Red Diamond Nectarine (U.S. Plant Pat. No. 3,165), by producing freestone nectarines that are full red in skin color and very firm in texture, but is distinguished therefrom and an improvement thereon by producing fruit that ripens 3 days later, is larger in size, is crispier in texture, and has a yellow pit cavity that tightly surrounds the stone.

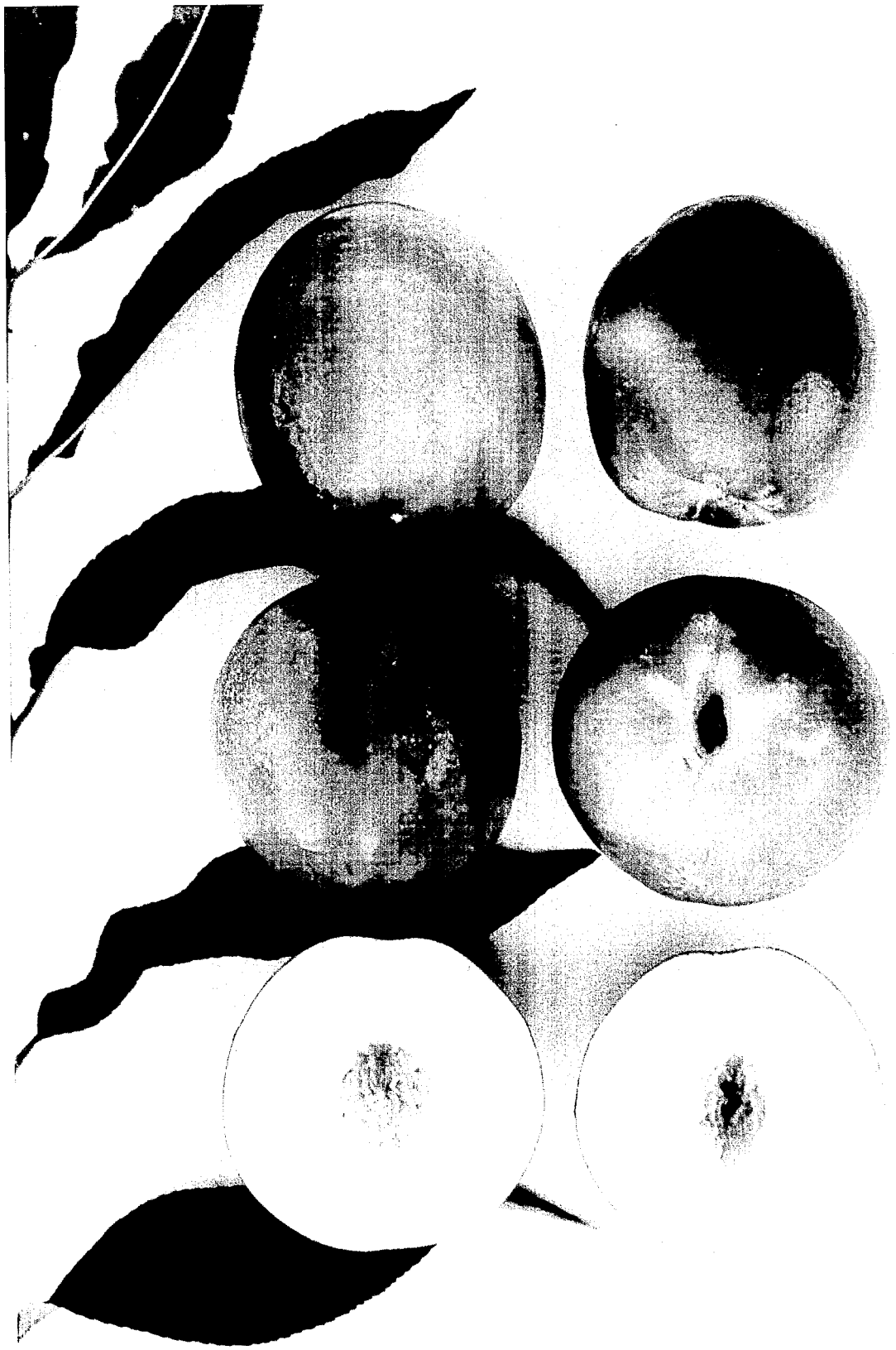

* * * * *